United States Patent
Hardert

(10) Patent No.: US 8,366,734 B2
(45) Date of Patent: Feb. 5, 2013

(54) ULTRAVIOLET BONDED OCCLUSION BALLOON

(75) Inventor: Michael W. Hardert, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1070 days.

(21) Appl. No.: 11/831,382

(22) Filed: Jul. 31, 2007

(65) Prior Publication Data

US 2008/0033480 A1  Feb. 7, 2008

Related U.S. Application Data

(60) Provisional application No. 60/834,630, filed on Aug. 1, 2006.

(51) Int. Cl.
*A61M 29/00* (2006.01)
(52) U.S. Cl. ................................. 606/195
(58) Field of Classification Search .......... 606/191–195; 604/103.01, 180
See application file for complete search history.

(56) References Cited

U.S. PATENT DOCUMENTS

| | | | |
|---|---|---|---|
| 4,638,803 A | 1/1987 | Rand | |
| 4,819,637 A * | 4/1989 | Dormandy et al. | 606/195 |
| 5,041,090 A | 8/1991 | Scheglov et al. | |
| 5,092,841 A | 3/1992 | Spears | |
| 5,591,199 A | 1/1997 | Porter et al. | |
| 5,925,060 A | 7/1999 | Forber | |
| 6,293,960 B1 | 9/2001 | Ken | |
| 6,299,597 B1 * | 10/2001 | Buscemi et al. | 604/101.03 |
| 6,346,117 B1 | 2/2002 | Greenhalgh | |
| 6,350,270 B1 | 2/2002 | Roue | |
| 6,547,804 B2 * | 4/2003 | Porter et al. | 606/195 |
| 6,855,153 B2 | 2/2005 | Saadat | |
| 7,338,511 B2 * | 3/2008 | Mirigian et al. | 606/200 |
| 8,231,666 B2 * | 7/2012 | Kim et al. | 623/1.11 |
| 2002/0165572 A1 | 11/2002 | Saadat | |
| 2004/0039242 A1 * | 2/2004 | Tolkoff et al. | 600/9 |

* cited by examiner

*Primary Examiner* — Gary Jackson
*Assistant Examiner* — Eric Blatt
(74) *Attorney, Agent, or Firm* — Brinks Hofer Gilson & Lione

(57) ABSTRACT

An embolization device for occluding a body vessel cavity defined by a cavity wall is disclosed. The device includes an inflatable balloon made of a permeable material. The balloon is configured to have a deflated state and an inflated state and includes a proximal portion having an inflation hole formed therethrough to a cavity within the balloon. An inflation member is removably attached to the proximal portion and is configured to introduce a material in the cavity by way of the hole for inflation of the balloon. The permeable material is configured to allow inflation of the balloon and a portion of the solidifiable material to pass through the permeable material for contact with the cavity wall. The inflation member is configured to transmit, for example, ultra violet light to cure a solidifiable material, thereby maintaining the balloon in the inflated state and to adhering the balloon to the cavity wall.

21 Claims, 5 Drawing Sheets

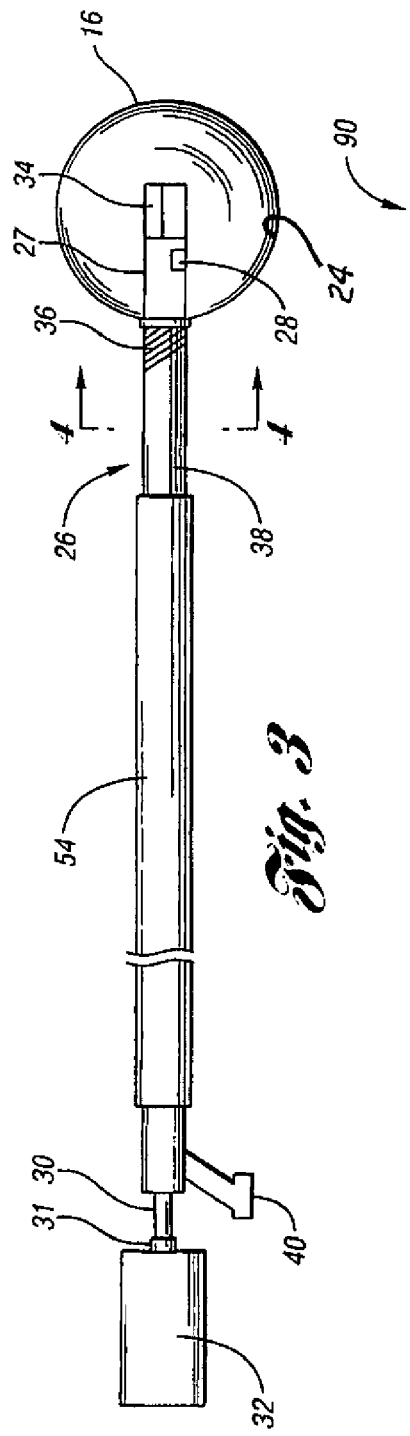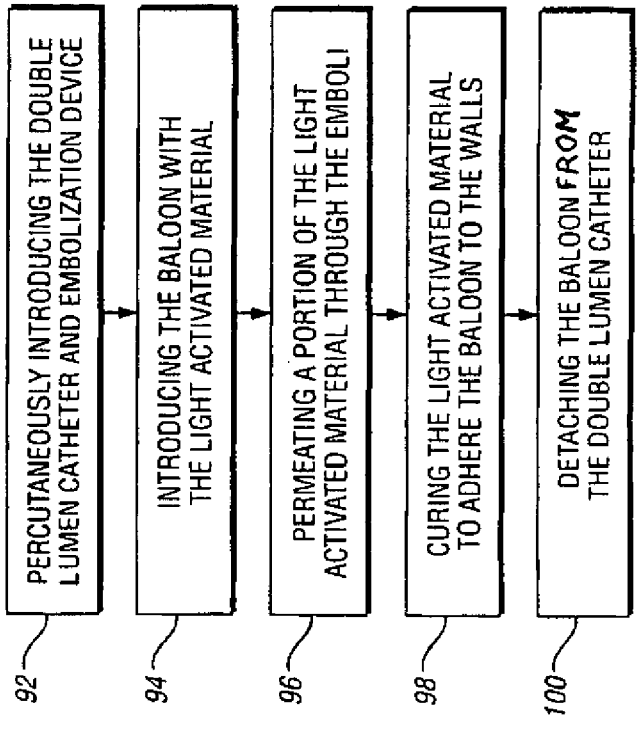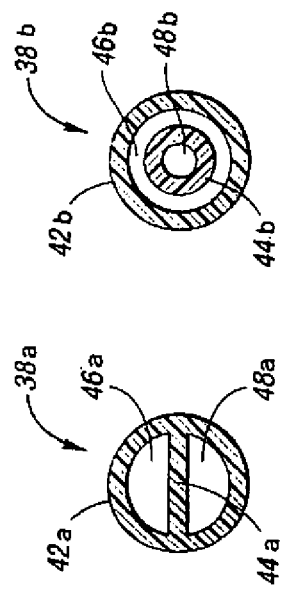

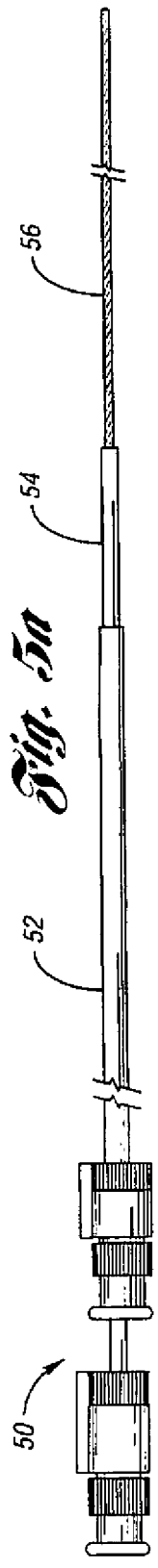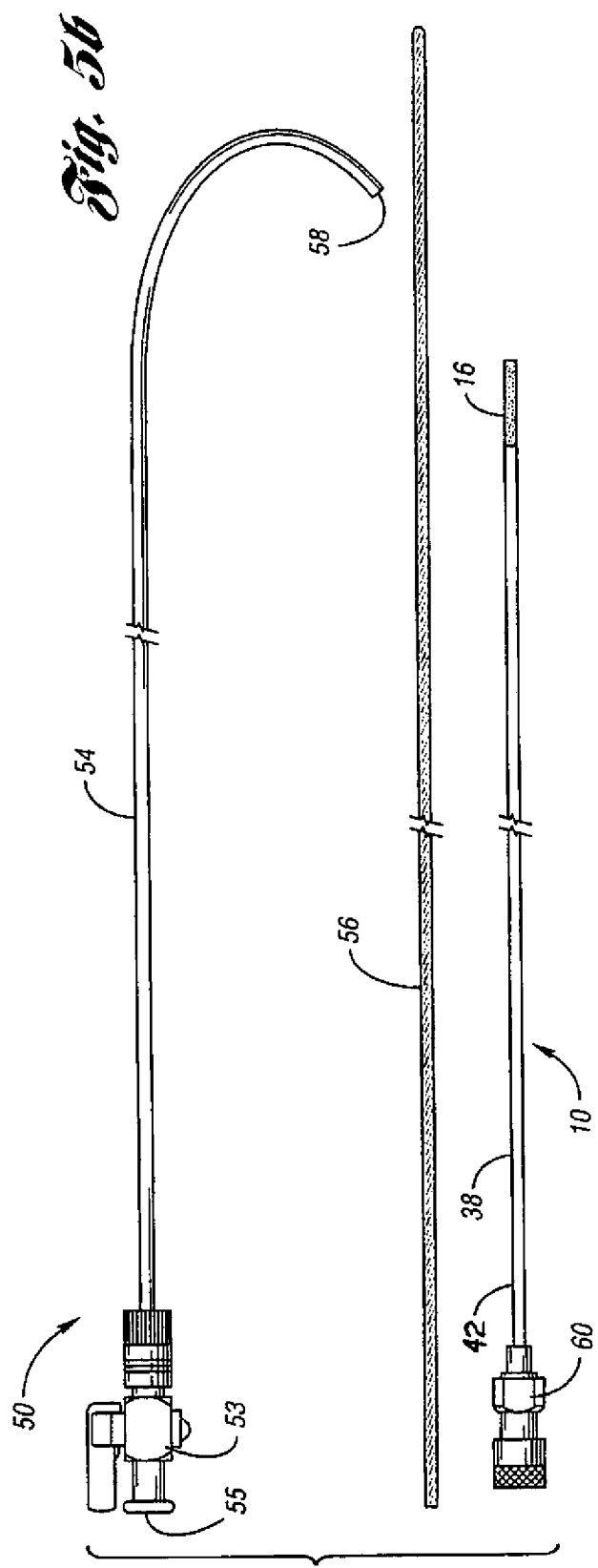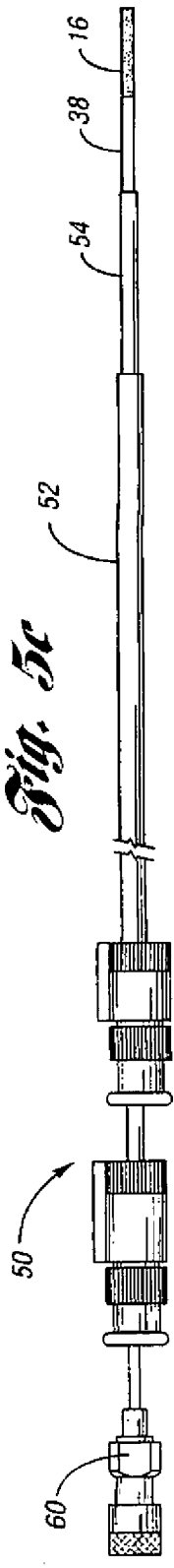

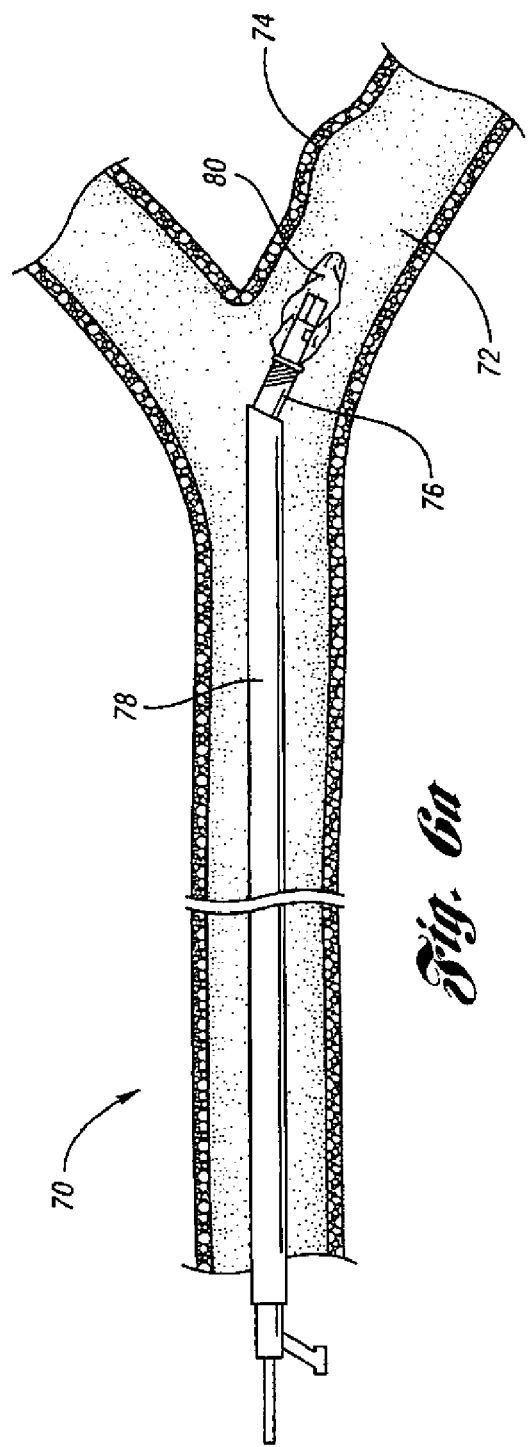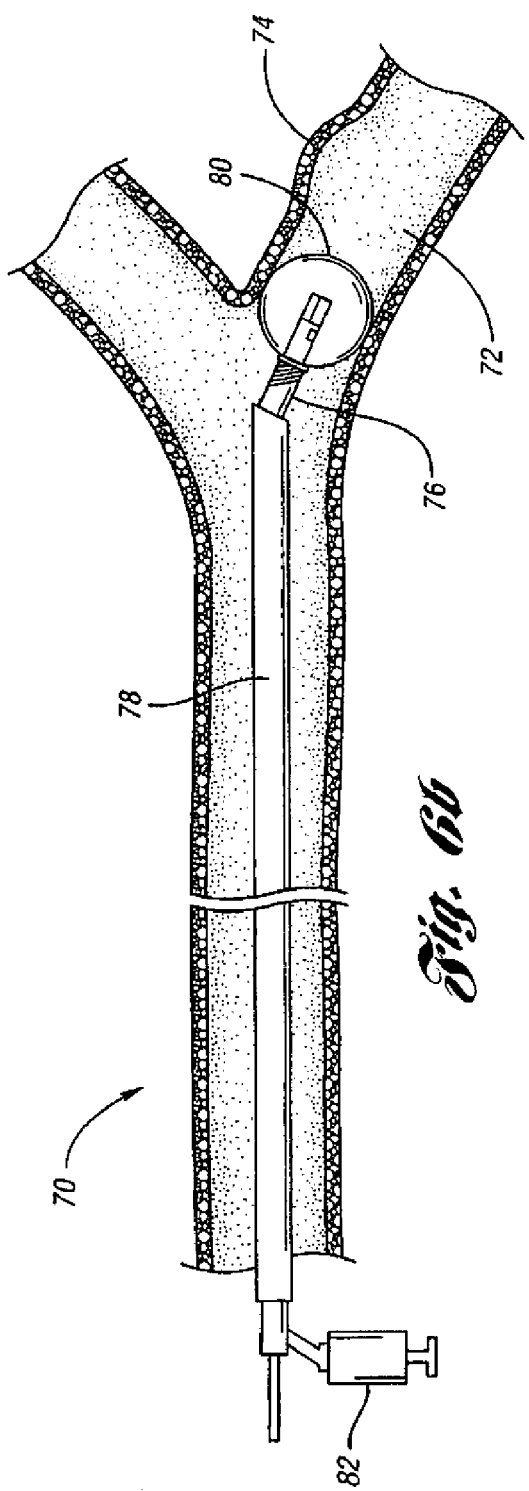

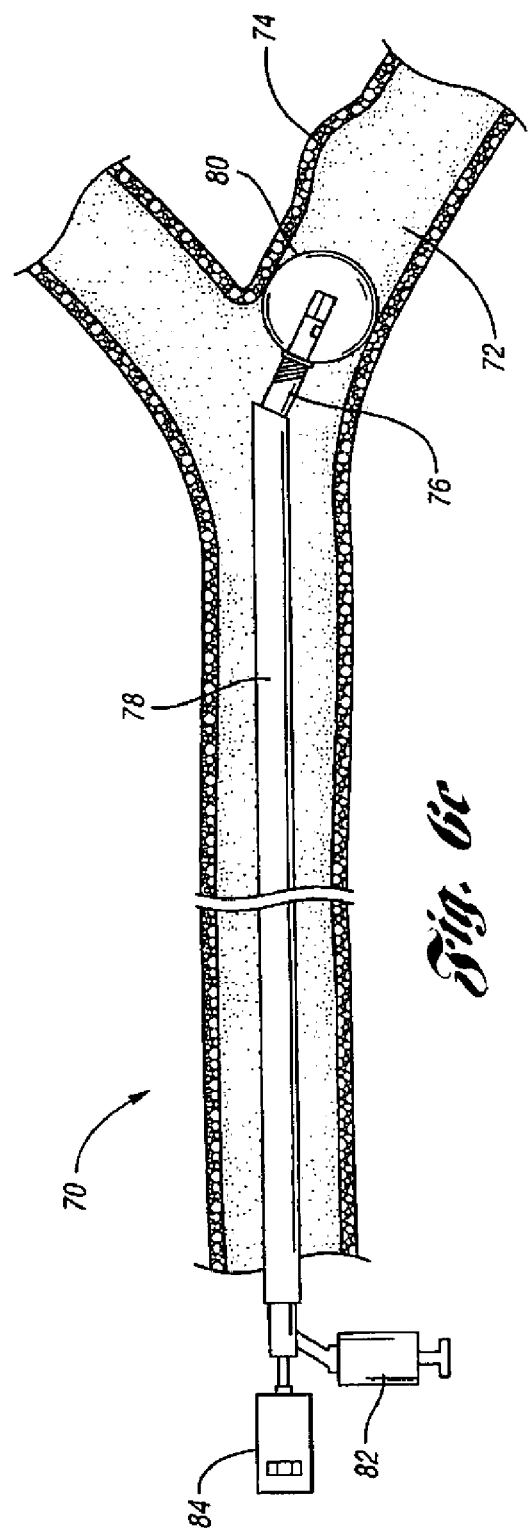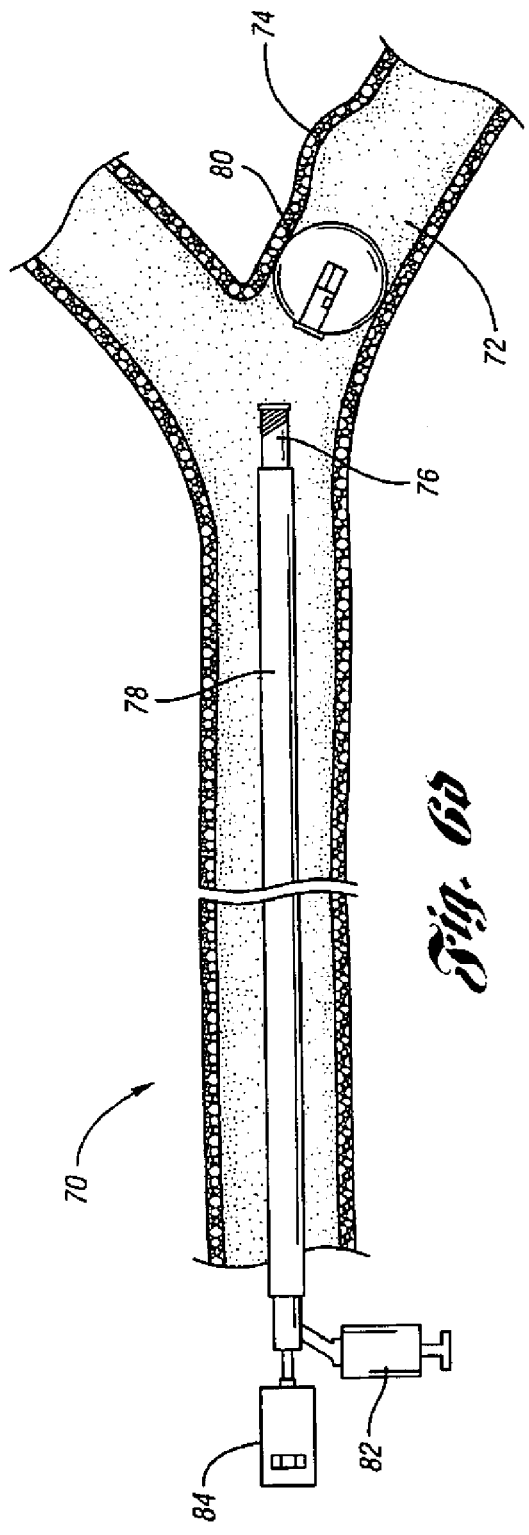

ULTRAVIOLET BONDED OCCLUSION BALLOON

CROSS-REFERENCE TO RELATED APPLICATIONS

This application claims the benefit of U.S. Provisional Application Ser. No. 60/834,630, filed on Aug. 1, 2006, entitled "Ultraviolet Bonded Occlusion Balloon," the entire contents of which are incorporated herein by reference.

BACKGROUND OF THE INVENTION

1. Field of the Invention

The present invention relates to medical devices. More particularly, the present invention relates to embolization devices and methods for occluding a body vessel cavity such as a blood vessel.

2. Description of Related Art

In certain procedures, for example the treatment of aneurisms, it is desirable to embolize, or block off, body vessel cavities such as blood vessels. Currently, there are a number of devices for embolizing blood vessels including embolization coils. Embolization coils use a wire usually bent into a coil shape to create an obstruction in the blood vessel on which a blood clot can form, leading to occlusion of the blood vessel. However, the blood clot forms relatively slowly over time, meaning embolization coils do not seal off the blood vessel instantly. As a result, it takes additional time for the treatment to take effect, exposing the patient to greater risk of, in this case, rupture of the aneurism.

In view of the above, it is apparent that there exists a need for an improved embolization device and method for occluding a body cavity vessel.

BRIEF SUMMARY OF THE INVENTION

In satisfying the above need, as well as overcoming the enumerated drawbacks and other limitations of the related art, the present invention provides an embolization device for occluding a body vessel cavity defined by a cavity wall. The device includes an inflatable balloon made of a permeable material. The balloon is configured to have a deflated state and an inflated state and includes a proximal portion having an inflation hole formed there through to a cavity within the balloon. An inflation member is removably attached to the proximal portion and is configured to introduce a solidifiable material in the cavity by way of the hole for inflation of the balloon. The permeable material is configured to allow inflation of the balloon and a portion of the solidifiable material to pass through the permeable material for contact with the cavity wall. The inflation member is configured to transmit light to cure the solidifiable material, thereby maintaining the balloon in the inflated state and adhering the balloon to the cavity wall.

More specifically, the inflation member includes a double lumen catheter including an inner wall disposed within an outer wall defining a first lumen and a second lumen. The first lumen is configured to introduce the solidifiable material into the cavity within the balloon. The second lumen is disposed about a fiber optic cable configured to transmit light to the solidifiable material and having a first end attached to a light source and a second end configured to transmit light to the cavity within the balloon. The second end of the fiber optic cable may be attached to a light diffusion device disposed within the cavity of the balloon, the light diffusion device being configured to diffuse light from the light source, for example, using a prism. In some embodiments, the inner wall and second lumen are coaxial with the outer wall and first lumen.

In one embodiment of the present invention, the inflation member is configured to transmit ultraviolet light.

In another embodiment of the present invention, the balloon is made of a polyester and platinum mesh. The balloon is also sized to fit within the wall of the body cavity vessel in the deflated state and contact the walls in the inflated state.

In yet another embodiment of the present invention, the solidifiable material is an adhesive material. The adhesive material includes at least one of the following materials: ultraviolet light curing adhesive, moisture curing adhesive, and fast curing adhesive.

In addition, the present invention includes a method of occluding a body cavity vessel having a body wall, the method includes inflating a balloon with a solidifiable material, permeating a portion of the solidifiable material through the balloon, and curing the solidifiable material to adhere the balloon to the body wall. The method also includes delivering the balloon to the body cavity vessel using the inflation member and transmitting light to the balloon to cure the solidifiable material. The method further encompasses forming a solid emboli by curing the solidifiable material, adhering the solid emboli to the body wall by curing the solidifiable material for occlusion of the body cavity vessel, detaching the solid emboli from the inflation member, and removing the inflation member from the body cavity vessel.

Further objects, features, and advantages of the present invention will become apparent from consideration of the following description and the appended claims when taken in connection with the accompanying drawings.

BRIEF DESCRIPTION OF THE DRAWINGS

FIG. 3 is a side view of the embolization device of FIG. 1 attached to a double lumen catheter;

FIG. 4a is a section view along the line 4-4 of FIG. 3 showing one embodiment of the double lumen catheter;

FIG. 4b is a section view along a line 4-4 of FIG. 3 showing an alternate embodiment of the double lumen catheter;

FIG. 5a is a side view of an embolization assembly for occluding a body vessel cavity for treatment of, for example, an aneurism in accordance with one embodiment of the present invention;

FIG. 5b is an exploded side view of the assembly in FIG. 5a;

FIG. 5c is a side view of the embolization assembly of FIG. 5a showing the embolization device in position within the embolization assembly;

FIGS. 6a-6d are environmental views of each step of one method of occluding a body vessel cavity using the embolization assembly of FIG. 4a; and FIG. 7 is a flow chart of the method of occluding a body vessel cavity shown in FIGS. 6a-6d.

DETAILED DESCRIPTION OF THE INVENTION

Figure 1:
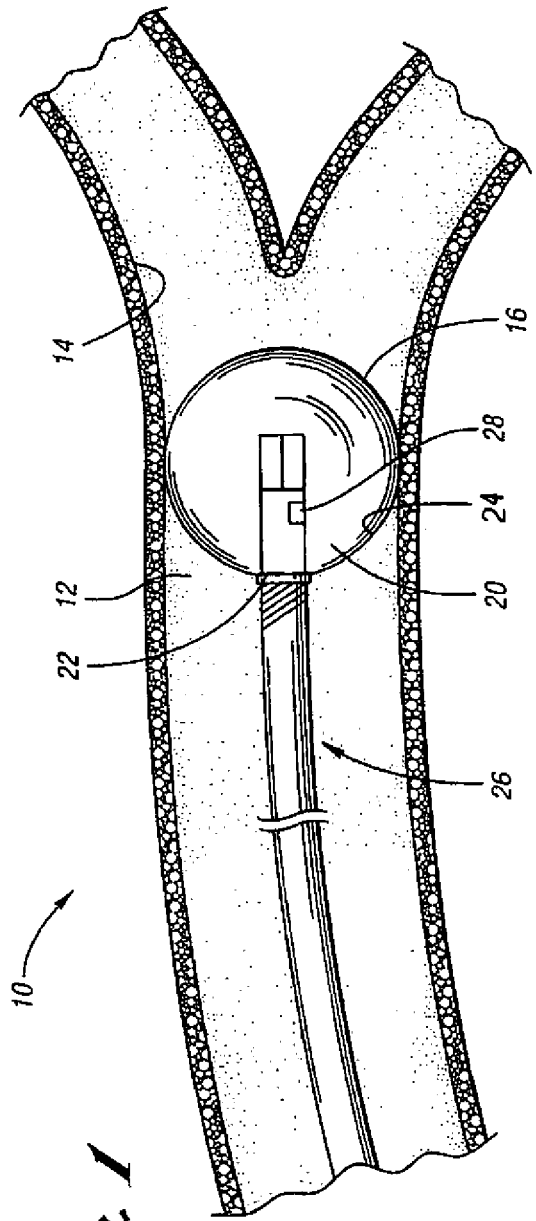
FIG. 1 is an environmental view of the embolization device in accordance with one embodiment of the present invention.

Referring now to the drawings, an embolization device embodying the principles of the present invention is illustrated in FIG. 1 and designated at 10. As shown in FIG. 1, the embolization device 10 is disposed within a body cavity 12 defined by a cavity wall 14. As its primary components, the embolization device 10 includes an inflatable balloon 16 and an inflation member 26. The balloon 16 is made of a permeable material and includes a proximal portion 20 having an inflation hole 22, leading to a balloon cavity 24. The inflation member 26 is removably attached to the proximal portion 20 of the balloon 16 through the inflation hole 22.

Figure 2B:
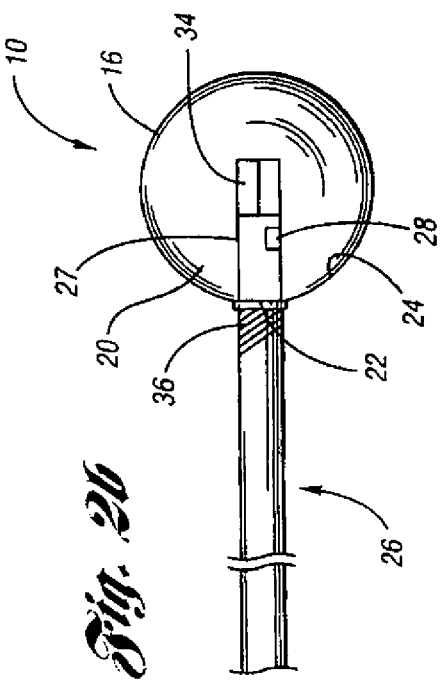
FIG. 2b is a side view of the embolization device of FIG. 1 in an inflated state.
Figure 2A:
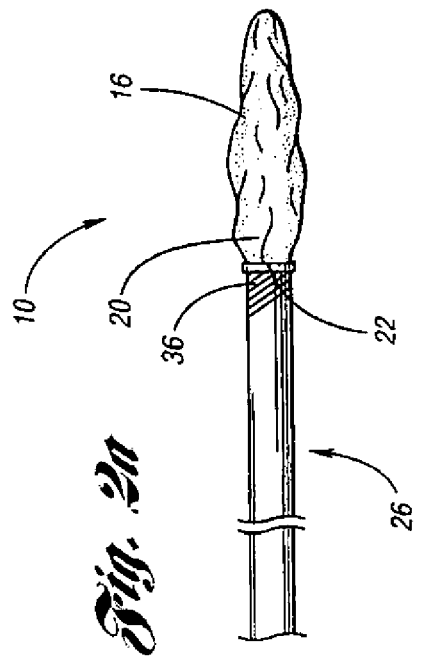
FIG. 2a is a side view of the embolization device of FIG. 1 in a deflated state.

FIGS. 2a and 2b illustrate the balloon 16 outside of the body cavity 12 in a deflated state (FIG. 2a) and an inflated state (FIG. 2b). The balloon 16 is sized differently for each application, depending on the size of the body cavity 12 in which it is to be used, but is sized to fit within the cavity wall 14 when in the deflated state and to contact the cavity wall 14 when in the inflated state. The balloon 16 is inflated via the inflation member 26 introducing a solidifiable material into the balloon cavity 24 by way of the inflation hole 22. The solidifiable material is introduced through an inflation port 28 near a distal end 27 of the inflation member 26, inflating the balloon 16 as the solidifiable material fills the balloon cavity 24.

The permeable material may be any appropriate material capable of allowing inflation of the balloon and a portion of the solidifiable material to pass through the permeable material to form a thin layer on an exterior of the balloon 16. In one embodiment, the permeable material may be, for example, a polyester and platinum mesh where the mesh is sized to have the above characteristics. As a result, when the balloon 16 is positioned within the body cavity 12 and inflated, the thin layer of solidifiable material comes into contact with the cavity wall 14. Once inflated and in contact with the cavity wall 14, the solidifiable material is cured. In the present embodiment the inflation member 26 transmits light to the balloon cavity 24 to cure the solidifiable material. This maintains the balloon 16 in the inflated state, forming a solid emboli, and adheres the balloon 16 to the cavity wall 14. This occludes the body cavity 12 with relative speed compared to the prior art.

FIG. 3 illustrates a preferred embodiment of the present invention, where the inflation member 26 is configured as a double lumen catheter 38. In FIGS. 4a and 4b two embodiments of the double lumen catheter 38 are illustrated and include an inner wall 44a or 44b disposed within an outer wall 42a or 42b arranged to define a first lumen 46a or 46b and a second lumen 48a or 48b. In each embodiment of FIGS. 4a and 4b, the first lumen 46a (and 46b) provides the passage through which the solidifiable material is conducted into the balloon cavity 24 (see FIG. 2b) and the second lumen 48a (and 48b) is configured to transmit light to the solidifiable material. In the embodiment of the double lumen catheter 38a shown in FIG. 4a, the walls 42a and 44b are arranged such that the first and second lumen's 46a and 48a are side-by-side within the outer wall 42a. In the alternate embodiment shown in FIG. 4b, the inner wall 44b is arranged coaxially within the outer wall 42b, defining coaxial first and second lumen's 46b and 48b. In either embodiment, the solidifiable material is provided to the first lumen 46b via an injection hub 40 (see FIG. 3).

Returning to FIG. 3, the double lumen catheter 38 is arranged to transmit light to the solidifiable material within the balloon cavity 16 by disposing a fiber optic cable 30 within the second lumen 48b (in FIG. 4b). The fiber optic cable 30 includes a first end 31 attached to a light source 32 and a second end extending to the distal end 27 of the inflation member 26 within the balloon cavity 24. Light from the light source 32 is then transmitted via the fiber optic cable 30 into the balloon cavity 24.

The distal end 27 of the inflation member 26 includes a light diffusion device 34 and the aforementioned inflation port 28. According to the present embodiment, when the inflation member 26 is attached to the balloon 16, the light diffusion device 34 is disposed substantially within the center of the balloon cavity 24. The light diffusion device 34 is configured to diffuse light provided by the fiber optic cable 30 from the light source 32 in multiple directions within the balloon cavity 24 and may include, for example, a prism.

Once the solidifiable material is cured, the embolization device 10 may be detached from the inflation member 26 by means of release threads 36. Rotation of the inflation member 26 may unscrew the release threads 36 from the proximal portion 20 of the inflatable balloon 16, freeing the inflation member 26 and permitting its removal from the body cavity 12 while leaving the embolization device 10 secured firmly in place. The release threads 36 are but one example of a coupler for attaching the inflation member 26 to the inflatable balloon 16. Other examples may include, but are not limited to, friction-based couplers, spring based couplers or may include other similar features. In the present embodiment, the distal end 27 of the inflation member 26, including the light diffusion device 34, is permanently secured within the balloon cavity 24 after the solidifiable material is cured. Thus, the distal end 27 of the inflation member 26 of the present embodiment is also detachable from the inflation member 26. As a result, when the embolization device 10 is detached from the inflation member 26, the distal end 27 remains secured by the solidifiable material within the balloon cavity 24 (see FIG. 6d).

In a preferred embodiment, the solidifiable material is an adhesive material, such as an ultraviolet light curing adhesive. As a result, the light source 32 is configured to provide ultraviolet light which is subsequently transmitted through the second lumen, via the fiber optic cable 30, to the balloon cavity 24 in order to cure the ultraviolet light curing adhesive.

However, other embodiments may use other adhesive materials, for example, a moisture curing adhesive or a fast curing adhesive. In the latter two cases, it may not be necessary to provide light to cure the adhesive and maintain the balloon 16 in the inflated state and adhere it to the cavity wall 14. In these alternate embodiments, exposure of the adhesive to moisture in the body cavity 12, or simply waiting a prescribed period of time after inflation of the balloon 16, may be sufficient to cure the adhesive without the transmission of light.

FIGS. 5a, 5b and 5c depict an embolization assembly 50 for occluding a body cavity, for example, to treat an aneurism in a body vessel in accordance with another embodiment of the present invention. As shown, the embolization assembly 50 comprises the double lumen catheter 38 described above attached to the inflatable balloon 16 for inflation of the balloon 16 at an occlusion site. In this embodiment, the assembly 50 includes the embolization device 10 mentioned above. The outer wall 42 of the double lumen catheter 38 is preferably made of a soft flexible material such as silicon or any other suitable material and may include a first lumen 46 and a second lumen 48. The first lumen 46 may be in fluid communication with the balloon 16 for inflating and deflating the balloon. The second lumen 48 may be formed therethrough for the transmission of light to the balloon cavity 24 (see FIGS. 1-3).

As shown, the assembly 50 further includes a guide catheter 54 having a distal end 52 through which the double lumen catheter 38 is disposed for deployment in the body vessel. The guide catheter 54 is preferably made of a soft, flexible material such as silicon or any other suitable material. Generally, the guide catheter 54 further has a proximal end 55 and a plastic adaptor or hub 53 to receive the embolization device 10 and double lumen catheter 38 to be advanced therethrough. The size of the guide catheter 54 is based on the size of the body vessel in which it percutaneously inserts, and the size of the double lumen catheter 38.

As shown, the assembly 50 may also include a wire guide 56 configured to be percutaneously inserted within the vasculature to guide the guide catheter 54 to the occlusion target area. The wire guide 56 provides the guide catheter 54 a path during insertion within the body cavity 12. The size of the wire guide 56 is based on the inside diameter of the guide catheter 54.

In one embodiment, the double lumen catheter 38 has a proximal fluid hub 60 in fluid communication with the balloon 16 via the first lumen 46 for fluid to be passed therethrough for inflation of the balloon 16 during the embolization procedure. The fluid hub 60 may be attached to the injection hub 40 (see FIG. 3) through which the fluid is injected.

As shown, the embolization device 10 is coaxially disposed through the guide catheter 54, following removal of the wire guide 56, in order to position the inflatable balloon 16 in position for occlusion of the body vessel. The embolization device 10 is guided through the guide catheter 54 preferably from the hub 53 and exiting from the distal end 58 of the guide catheter 54 to a location within the vasculature where embolization is desired.

In this embodiment, the apparatus further includes a polytetrafluoroethylene (PTFE) introducer sheath 52 for percutaneously introducing the wire guide 56 and the guide catheter 54 in a body vessel. Of course, any other suitable material may be used without falling beyond the scope or spirit of the present invention. The introducer sheath 52 may have any suitable size, e.g., between about three-french to eight-french. The introducer serves to allow the guide catheter 54 and double lumen catheter 38 to be percutaneously inserted to a desired location in the body vessel. The introducer sheath 52 receives the guide catheter 54 and provides stability to the guide catheter 54 at a desired location of the body vessel. For example, the introducer sheath 52 is held stationary within a common visceral artery, and adds stability to the guide catheter 54, as the guide catheter 54 is advanced through the introducer sheath 52 to a desired occlusion area in the vasculature.

When the distal end 58 of the guide catheter 54 is at the desired location in the body vessel, the wire guide 56 is removed and the embolization device 10 including the double lumen catheter 38 is inserted therethrough to the occlusion area. The double lumen catheter 38 is advanced through the guide catheter 54 for deployment through its distal end 58. In this embodiment, when the device 10 is located within the desired occlusion area, solidifiable material (e.g. ultraviolet light curing adhesive) may be passed through the fluid hub 60, through the first lumen 46 and into the balloon cavity 24 of the embolization device 10, mechanically inflating the balloon 16. In the inflated state, the balloon 16 is configured to engage the wall of the body vessel wherein the solidifiable material is cured, adhering the balloon 16 to the wall and occluding the body vessel.

It is understood that the assembly described above is merely one example of an assembly that may be used to deploy the embolization device 10 in the body vessel. Of course, other apparatus, assemblies and systems may be used to deploy any embodiment of the embolic protection device without falling beyond the scope or spirit of the present invention.

FIGS. 6a, 6b, 6c, and 6d illustrate one method 70 for occluding a vessel to treat, for example, an aneurism 74 in a body vessel 72, implementing the assembly mentioned above. The method 70 comprises percutaneously introducing a double lumen catheter 76 having an inflatable balloon 80 through a guide catheter 78 for embolization of the body vessel 72 (see FIG. 6a). Introduction of the double lumen catheter 76 may be performed by any suitable means or mechanism. As mentioned above, an introducer sheath and a wire guide may be used to provide support and guidance to the double lumen catheter 76. For example, the wire guide may be percutaneously inserted through the introducer sheath to a desired location in the body vessel 72. The guide catheter 78 may then be placed over the wire guide for percutaneous guidance and introduction of the guide catheter 78 to the target location. The wire guide may then be removed and replaced with the double lumen catheter 76.

The method 70 further comprises inflating the balloon 80 of the embolization device using solidifiable material 82 introduced through the double lumen catheter 76. As shown in FIG. 6a, the balloon 80 is positioned at the target area in its deflated state. Introduction of the solidifiable material 82, in this case ultraviolet light curing adhesive, causes the balloon 80 to inflate and contact walls of the body vessel 72 (see FIG. 6b). The balloon 80 is made of a permeable material that permits inflation of the balloon and allows a portion of the solidifiable material to pass through the material and contact the walls.

The method 70 also includes curing the solidifiable material 82 as shown in FIG. 6c. In this example, the ultraviolet light is provided by an ultraviolet light source 84. The ultraviolet light is transmitted through the double lumen catheter 76 to a cavity within the balloon 80, curing the ultraviolet light curing adhesive and maintaining the balloon 80 in the inflated state and adhering it to the walls. This essentially forms a solid emboli within the body vessel 72. As shown in FIG. 6d, the double lumen catheter 76 is subsequently detached from the balloon 80, and removed from the body vessel 72. However, the balloon 80 remains in place as a solid emboli occluding the body vessel 72.

FIG. 7 provides a flow chart designated at 90 summarizing the method described above for embolizing a body vessel. The method 90 includes percutaneously introducing the double lumen catheter and embolization device in the body vessel in box 92. It further includes inflating the balloon with the solidifiable material in box 94 and permeating a portion of the solidifiable material through the balloon in box 96. It also includes curing the solidifiable material to adhere the balloon to the walls of the body vessel in box 98 and includes detaching the balloon from the double lumen catheter to leave the balloon in place as a solid emboli to occlude the body vessel in box 100.

While the present invention has been described in terms of preferred embodiments, it will be understood, of course, that the invention is not limited thereto since modifications may be made to those skilled in the art, particularly in light of the foregoing teachings.

The invention claimed is:

1. An embolization device for occluding a body vessel defined by a vessel wall, the device comprising:
    an inflatable balloon comprised of a permeable material, the balloon being configured to have a deflated state and an inflated state and including a proximal portion having an inflation hole formed therethrough leading to a cavity within the balloon; and
    an inflation member removably attached to the proximal portion of the balloon through the inflation hole, the inflation member having a distal end disposed within the cavity and extending substantially toward a center of the cavity, the inflation member being configured to introduce a solidifiable material in the cavity by way of an inflation port near the distal end of the inflation member, the permeable material being configured to allow inflation of the balloon and a portion of the solidifiable material to pass through the permeable material for contact with the vessel wall, the distal end of the inflation member terminating with a light diffusion member configured to transmit light to the solidifiable material to maintain the balloon in the inflated state and to adhere the balloon to the vessel wall, the inflation port disposed along the inflation member proximal relative to the light diffusion member, the distal end of the inflation member being detachable from the inflation member.

2. The device of claim 1 wherein the inflation member comprises a double lumen catheter including an inner wall to define a first lumen and an outer wall disposed about the inner wall to define a second lumen, the second lumen being configured to introduce the solidifiable material into the cavity within the balloon and the first lumen being configured to transmit light to the solidifiable material.

3. The device of claim 2 wherein the inner wall is coaxial with the outer wall.

4. The device of claim 2 wherein the first lumen includes a fiber optic cable having a first end and a second end, the first end attached to a light source and the light diffusion member configured to diffuse light provided by the fiber optic cable at the second end to the cavity within the balloon.

5. The device of claim 1 wherein the diffusion member is a prism.

6. The device of claim 1 wherein the inflation member is configured to transmit ultraviolet light.

7. The device of claim 1 wherein the balloon is made of a polyester and platinum mesh.

8. The device of claim 1 wherein the balloon is sized to fit within the wall of the body vessel in the deflated state and contact the wall in the inflated state.

9. The device of claim 1 wherein the solidifiable material comprises an adhesive material.

10. The device of claim 9 wherein the adhesive material comprises at least one of the following materials: ultraviolet light curing adhesive, moisture curing adhesive, and fast curing adhesive.

11. An embolization device for occluding a body vessel defined by a vessel wall, the device comprising:
an inflatable balloon comprised of a permeable material, the balloon being configured to have a deflated state and an inflated state and sized to fit within the wall of the body vessel in the deflated state and sized to contact the wall of the body vessel in the inflated state, and further including a proximal portion having an inflation hole formed therethrough leading to a cavity within the balloon; and
a double lumen catheter removably attached to the proximal portion of the balloon through the inflation hole, the double lumen catheter having a distal end disposed within the cavity, the double lumen catheter including an inner wall to define a first lumen and an outer wall disposed about the inner wall to define a second lumen, the second lumen being configured to introduce a solidifiable material into the cavity by way of an inflation port near the distal end of the double lumen catheter, the permeable material being configured to allow inflation of the balloon and a portion of the solidifiable material to pass through the permeable material, the first lumen including a fiber optic cable, the fiber optic cable including a first end attached to a light source and a second end extending to the distal end of the double lumen catheter within the cavity configured to transmit light to the solidifiable material in the cavity to maintain the balloon in the inflated state and to adhere the balloon to the vessel wall, the distal end of the double lumen catheter being detachable from the double lumen catheter.

12. The device of claim 11 wherein the solidifiable material comprises an adhesive material cured by ultraviolet light.

13. The device of claim 11 wherein the fiber optic cable is configured to transmit ultraviolet light.

14. The device of claim 11 wherein the distal end of the double lumen catheter terminates with a light diffusion member disposed within the cavity of the balloon, the inflation port disposed along the inflation member proximal relative to the light diffusion member, the light diffusion member being configured to diffuse light from the light source provided by the second end of the fiber optic cable.

15. The device of claim 14 wherein the light diffusion member is a prism.

16. The device of claim 11 wherein the balloon is made of a polyester and platinum mesh.

17. A method of occluding a body vessel having a body wall, the method comprising:
delivering an inflatable balloon to the body vessel using an inflation member removably attached thereto, the inflation member having a distal end disposed within a cavity of the balloon, the distal end of the inflation member terminating with a light diffusion member;
introducing a solidifiable material into the balloon cavity through an inflation port near the distal end of the inflation member to inflate the balloon, the inflation port disposed along the inflation member proximal relative to the light diffusion member, the inflatable balloon being comprised of a permeable material;
permeating a portion of the solidifiable material through the balloon to engage the balloon with the body wall;
transmitting light to the balloon through the light diffusion member to cure the solidifiable material to maintain the balloon in an inflated state and adhere the balloon to the body wall; and
detaching the balloon from the inflation member, wherein the inflation member detaches from the distal end thereof.

18. The method of claim 17 further comprising forming a solid emboli by curing the solidifiable material.

19. The method of claim 18 further comprising:
adhering the solid emboli to the body wall by curing the solidifiable material for occlusion of the body vessel.

20. The device of claim 11 wherein the detachable distal end of the double lumen catheter is disposed substantially within the center of the balloon cavity.

21. The device of claim 4 wherein the light diffusion member is configured to diffuse light from the light source provided by the fiber optic cable.

* * * * *